(12) United States Patent
Eklund et al.

(10) Patent No.: US 10,053,420 B2
(45) Date of Patent: Aug. 21, 2018

(54) PROCESSES FOR THE PREPARATION OF COMPOUNDS, SUCH AS 3-ARYLBUTANALS, USEFUL IN THE SYNTHESIS OF MEDETOMIDINE

(71) Applicant: Cambrex Karlskoga AB, Karlskoga (SE)

(72) Inventors: Lars Eklund, Karlskoga (SE); Margus Eek, Tallin (EE); Ramesh Ekambaram, Tallin (EE); Ants Maasalu, Tallin (EE)

(73) Assignee: Cambrex Karlskoga AB (SE)

( * ) Notice: Subject to any disclaimer, the term of this patent is extended or adjusted under 35 U.S.C. 154(b) by 0 days.

(21) Appl. No.: 15/547,288

(22) PCT Filed: Jan. 29, 2016

(86) PCT No.: PCT/GB2016/050204
§ 371 (c)(1),
(2) Date: Jul. 28, 2017

(87) PCT Pub. No.: WO2016/120635
PCT Pub. Date: Aug. 4, 2016

(65) Prior Publication Data
US 2018/0009744 A1    Jan. 11, 2018

(30) Foreign Application Priority Data
Jan. 30, 2015    (GB) .................................. 1501593.6

(51) Int. Cl.
| | | |
|---|---|---|
| C07C 45/62 | (2006.01) | |
| C07C 309/24 | (2006.01) | |
| C07D 233/00 | (2006.01) | |
| C07C 45/45 | (2006.01) | |
| C07C 45/63 | (2006.01) | |
| C07F 9/14 | (2006.01) | |
| C07D 233/64 | (2006.01) | |
| C07C 249/02 | (2006.01) | |
| C07C 47/232 | (2006.01) | |
| C07C 47/24 | (2006.01) | |
| C07C 47/228 | (2006.01) | |

(52) U.S. Cl.
CPC .......... *C07C 309/24* (2013.01); *C07C 45/455* (2013.01); *C07C 45/62* (2013.01); *C07C 45/63* (2013.01); *C07C 249/02* (2013.01); *C07D 233/64* (2013.01); *C07F 9/1403* (2013.01); *C07C 47/228* (2013.01); *C07C 47/232* (2013.01); *C07C 47/24* (2013.01)

(58) Field of Classification Search
CPC ....... C07C 45/62; C07C 45/63; C07C 45/455; C07C 309/24; C07C 249/02; C07C 47/228; C07D 233/64
USPC ......................................................... 568/422
See application file for complete search history.

(56) References Cited

U.S. PATENT DOCUMENTS

| | | |
|---|---|---|
| 4,113,781 A | 9/1978 | Aquila et al. |
| 4,416,902 A | 11/1983 | Mookherjee et al. |
| 6,313,354 B1 | 11/2001 | Markert et al. |

FOREIGN PATENT DOCUMENTS

| | | |
|---|---|---|
| WO | 1998045237 A1 | 10/1998 |
| WO | 2012069422 A1 | 5/2012 |
| WO | 2012120070 A1 | 9/2012 |
| WO | 2012172120 A2 | 12/2012 |
| WO | 2013014428 A1 | 1/2013 |

OTHER PUBLICATIONS

Search report from International Application No. PCT/GB2016/050204, dated May 3, 2016.

*Primary Examiner* — Sikarl A Witherspoon
(74) *Attorney, Agent, or Firm* — Lerner, David, Littenberg, Krumholz & Mentlik, LLP

(57) ABSTRACT

There is provided a process for the preparation of a compound of formula (I) as defined herein, wherein said process comprises reacting a compound of formula (II) as defined s herein with one or more suitable Vilsmeier reagent.

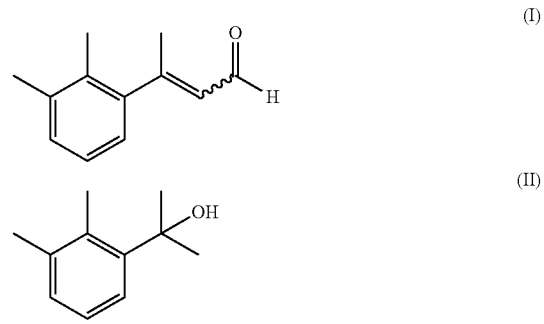

19 Claims, No Drawings

PROCESSES FOR THE PREPARATION OF COMPOUNDS, SUCH AS 3-ARYLBUTANALS, USEFUL IN THE SYNTHESIS OF MEDETOMIDINE

CROSS-REFERENCE TO RELATED APPLICATIONS

The present application is a national phase entry under 35 U.S.C. § 371 of International Application No. PCT/GB2016/050204 filed Jan. 29, 2016, which claims priority from GB 1501593.6 filed Jan. 30, 2015, all of which are incorporated herein by reference.

FIELD OF THE INVENTION

The present invention relates to new processes and new chemical compounds used in and obtained from such processes. In particular, it relates to new processes for the preparation of intermediates, such as 3-arylbutanals, useful in the synthesis of medetomidine.

BACKGROUND OF THE INVENTION

Compounds having a 3-arylbutanal core are particularly useful as intermediates in the production of medetomidine, which is a 4-substituted imidazole that is employed as the active ingredient in antifouling products such as Selektope™ and, in the form of the S enantiomer (known as dexmedetomidine), as a therapeutic agent.

However, the synthesis of the 3-arylbutanal core required for the production of medetomidine is hampered by the need for the incorporation of a sterically-hindered 2,3-dimethyl phenyl group.

The listing or discussion of an apparently prior-published document in this specification should not necessarily be taken as an acknowledgement that the document is part of the state of the art or common general knowledge.

Processes for the synthesis of medetomidine using 3-arylbutanals (specifically, 3-(2,3-dimethylphenyl) butanal) as synthetic intermediates are described in, for example, WO 2013/014428, which describes the synthesis of 3-arylbutanals via palladium catalysed coupling of a corresponding aryl boronate and croton aldehyde.

WO 2012/120070 describes the synthesis of 3-arylbutenals via palladium catalysed Heck coupling between a corresponding aryl halide and crotyl alcohol.

WO 2012/069422 describes the synthesis of 3-arylbutenals via reaction of an aryl lithium reagent with 4,4-dimethoxy-2-butanone.

Previous routes to 3-arylbutanals have also been based on processes involving the reaction of styrene derivatives with carbon monoxide and hydrogen, in the presence of a rhodium catalyst (see, for example, U.S. Pat. No. 4,113,781); and Lewis acid-catalysed reactions of benzyl acetals with vinyl ethers (see, for example, WO 98/045237).

Such processes have numerous technical and economic disadvantages, particularly when utilised in industrial manufacture, such as: the need for extreme reaction conditions (such as very low or very high temperatures and/or increased pressure); the generation of toxic waste products; the need for excessive dilution of reagents; the need for purification through removal of unwanted by-products; and the need to use toxic and/or expensive reagents.

DISCLOSURE OF THE INVENTION

We have now found that 3-arylbutanals may be prepared using a process comprising highly efficient formation of a corresponding 3-aryl butenal and selective reduction thereof.

In a first aspect of the invention, there is provided a process for the preparation of a compound of formula I

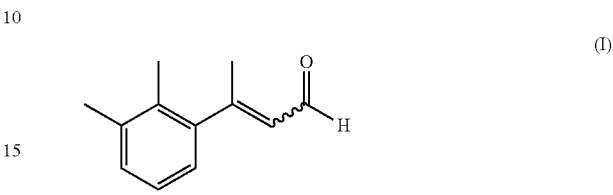

wherein said process comprises reacting a compound of formula II

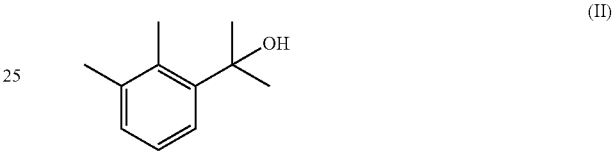

with one or more suitable Vilsmeier reagent.

The skilled person will understand that all references herein to particular aspects of the invention include references to all embodiments and combinations of one or more embodiments of that aspect of the invention. Thus, all embodiments of particular aspects of the inventions may be combined with one or more other embodiments of that aspect of the invention to form further embodiments without departing from the teaching of the invention.

The skilled person will understand that the term "Vilsmeier reagent" refers to a reagent suitable for performing the Vilsmeier-Haack reaction (also known as the Vilsmeier reaction and the Vilsmeier-Haack formylation), which reaction and reagents used therein are well-known in the art.

In particular, the skilled person will understand that a suitable Vilsmeier reagent will typically be formed by a reaction between a suitable amide (typically a N,N-disubstituted amide) and a suitable acid chloride.

Formation of the Vilsmeier reagent (i.e. by reaction between the amide and acid chloride) may be performed prior to conducting the formylation reaction (e.g. formylation comprised in the process of the first aspect of the invention), in which case the reagent may be referred to as a pre-formed Vilsmeier reagent, or may be performed in situ as part of the reaction (e.g. by mixture of a suitable amide and acid chloride as part of the process of the first aspect of the invention).

Suitable amides used in the formation of a Vilsmeier reagent typically include N-methyl formanilide, N,N-dimethyl formamide (also known as dimethylformamide or DMF). Other suitable amides that have been used in the formation of a Vilsmeier reagent include N-methyl formamide, N-formylpiperidine and N-formylindoline, unsubstituted formamide, N, N-dimethyl acetamide, N-methyl acetamide, N,N-dimethyl benzamide, pentamethyl acetamide, and the like.

Particular amides that may be mentioned include dimethylformamide.

Suitable acid chlorides used in the formation of a Vilsmeier reagent typically include phosphorous oxychloride ($POCl_3$) and oxalyl chloride ($(COCl)_2$). Other suitable acid chlorides that have been used in the formation of a Vilsmeier reagent include $COCl_2$, $SOCl_2$, $ClOCl$, $CH_3COCl$, $ArCOCl$, $ArSO_2Cl$, $PCl_5$, $Me_2NSO_2Cl$ and $RO_2CNHSO_2Cl$, where R represents a suitable, optionally substituted alkyl or aryl group, such as $C_{1-6}$ alkyl (e.g. methyl or ethyl) or phenyl), and Ar represents aryl, such as phenyl.

Particular acid chlorides that may be mentioned include oxalyl chloride and, more particularly, phosphorous oxychloride ($POCl_3$).

In a particular embodiment, the Vilsmeier reagent is formed (either pre-formed or formed in situ) by reaction of (i.e. combining, under suitable conditions) dimethylformamide and phosphorous oxychloride ($POCl_3$).

As used herein, references to a reagent or compound being formed in situ will be understood to refer to that reagent or compound being formed in the reaction vessel (i.e. the vessel in which the process as defined is being performed), rather than formed in a separate vessel and then added to the reaction vessel (which may be referred to as the compound or reagent being pre-formed).

In a more particular embodiment, the Vilsmeier reagent comprises a compound of formula IIIa and/or a compound of formula IIIb

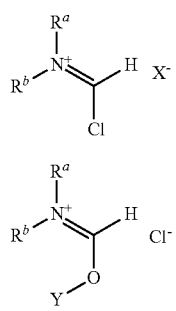

wherein:

X represents a counter ion derived from reaction with an acid chloride;

Y represent a substituent derived from reaction with an acid chloride;

each $R^a$ and $R^b$ independently represents H, $C_{1-3}$ alkyl or phenyl, or $R^a$ and $R^b$ taken together with the nitrogen to which they are attached form a pyrollidine, piperidine, morpholine or indoline moiety.

Unless otherwise specified, references to alkyl groups herein (such as $C_{1-6}$ alkyl and $C_{1-3}$ alkyl), may refer to groups that are straight-chain or, when there is a sufficient number (i.e. a minimum of three) of carbon atoms, be branched-chain. In particular, it may refer to groups that are straight chain (e.g. methyl and ethyl groups).

Unless otherwise specified, references to cycloalkyl groups used herein, may refer to groups that are wholly cyclic or, when there is a sufficient number (i.e. a minimum of four) part cyclic.

Unless otherwise specified, references to alkoxy groups herein (e.g. $C_{1-6}$ alkoxy) will be understood to refer to a similar alkyl group but which is bound at the point of attachment to the remainder of the molecule via an oxygen atom (such as a methoxy or ethoxy moiety).

The skilled person will understand that the reference to a counter ion derived from reaction with an acid chloride will refer to the counter ion generated during formation of the Vilsmeier reagent via reaction of a suitable amide (e.g. DMF) with an acid chloride (e.g. $POCl_3$). For example, where the suitable acid chloride used in the formation of the Vilsmeier reagent is $POCl_3$, X will represent —$PO_2Cl_2$.

The skilled person will understand that the reference to a substituent derived from reaction with an acid chloride will refer to the substituent generated during formation of the Vilsmeier reagent via reaction of a suitable amide (e.g. DMF) with an acid chloride (e.g. $POCl_3$). For example, where the suitable acid chloride used in the formation of the Vilsmeier reagent is $POCl_3$, Y will represent $POCl_2$.

Particular compounds of formulas IIIa and IIIb that may be mentioned include those wherein at least one of $R^a$ and $R^b$ is other than H.

More particular compounds of formulas IIIa and IIIb that may be mentioned include those wherein each $R^a$ and $R^b$ independently represents H, methyl or phenyl, or $R^a$ and $R^b$ taken together with the nitrogen to which they are attached form a piperidine or indoline moiety.

Yet more particular compounds of formulas IIIa and IIIb that may be mentioned include those wherein each $R^a$ and $R^b$ independently represents H, methyl or phenyl, provided that at least one of $R^a$ and $R^b$ is other than H, or $R^a$ and $R^b$ taken together with the nitrogen to which they are attached form a piperidine or indoline moiety.

Even more particular compounds of formulas IIIa and IIIb that may be mentioned include those wherein each $R^a$ and $R^b$ independently represents methyl or phenyl, or $R^a$ and $R^b$ taken together with the nitrogen to which they are attached form a piperidine or indoline moiety (e.g. a piperidine moiety).

In a more particular embodiment, the Vilsmeier reagent comprises a compound of formula IIIc and/or a compound of formula IIId

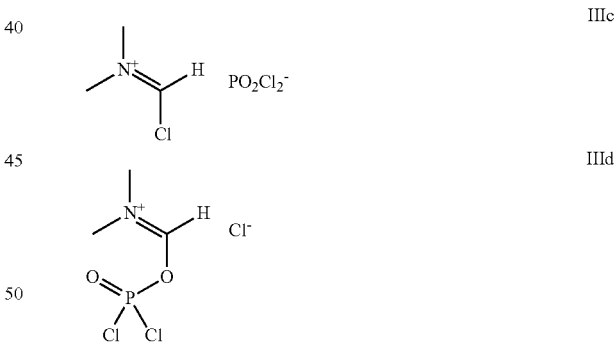

The skilled person will understand that the process of the first aspect of the invention may be performed in a suitable solvent, such as dimethylformamide (DMF). Where DMF is used as the solvent it may also act as a reagent (i.e. the amide component) in forming the required Vilsmeier reagent.

Thus, in a more particular embodiment, the Vilsmeier reagent is formed by reaction of dimethylformamide and $POCl_3$, optionally wherein dimethylformamide also acts as a solvent. In such embodiments, the skilled person will understand that the Vilsmeier reagent may be formed in situ by addition of the relevant acid chloride (e.g. $POCl_3$) to a reaction vessel containing a compound of formula II as defined herein and DMF (which may also be acting as a solvent).

The skilled person will understand that the process of the first aspect of the invention is a multi-step process, having a dehydration step and a formylation step.

Thus, in a particular embodiment of the first aspect of the invention, the process may be described as comprising the (concerted) steps of:

(i) reacting the compound of formula II to form a compound of formula IV

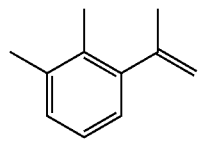

IV and subsequently (ii) reacting the compound of formula IV to form the compound of formula I.

The skilled person will further understand that these steps (i.e. steps (i) and (ii) directly above) will occur in a concerted manner in situ, i.e. in a single reaction vessel (which may be referred to as a one-pot process), with the compound of formula IV being a transient intermediate that is not isolated from the reaction mixture and not observed as a reaction product. In other words, these steps may occur in immediate succession.

Thus, in a more particular embodiment of the first aspect of the invention, the reaction is performed as a one-pot process (i.e. in a single reaction vessel) and/or (e.g. and) without isolation of a compound of formula IV.

The skilled person will understand that the compound of formula I may be obtained from the reaction mixture, and optionally purified, using techniques well-known in the art, such as via quenching of the reaction with an aqueous solution (such as an alkali solution, e.g. 4M NaOH) followed by extraction from the aqueous solution using a suitable organic solvent (such as an ether (e.g. MTBE) or, more particularly, toluene).

Thus, the process of the first aspect of the invention may be described as comprising the further step of isolating and optionally purifying the compound of formula I.

The skilled person will be able to adjust the reaction conditions (e.g. the temperature and/or pressure of the reaction) in order to obtain the desired product and/or maximise the yield thereof.

In a particular embodiments of the first aspect of the invention:

(I) the reaction (i.e. the concerted dehydration and formylation reaction, also described as steps (i) and (ii) above) may be performed at about atmospheric pressure (i.e. about 1 atm); and/or (II) the formation of the Vilsmeier reagent (e.g. the in situ) may be performed at reduced temperature (i.e. at a temperature below about 20° C.), such as at a temperature from about 0° C. to about 15° C.; and/or (III) following the formation of the Vilsmeier reagent, the reaction may be performed at increased temperature (i.e. at a temperature above about 20° C.), such as at a temperature from about 70° C. to about 90° C., e.g. at about 75° C. to about 85° C.

For example, in a particular embodiment the formation of the Vilsmeier reagent may be performed in situ (i.e. in the presence of the compound of formula II and the precursor to the Vilsmeier reagent, such as dimethylformamide) at reduced temperature (i.e. at a temperature below about 20° C.), such as at a temperature from about 0° C. to about 15° C.

In an alternative embodiment, the formation of the Vilsmeier reagent may be performed in situ (i.e. in the presence of the compound of formula II and the precursor to the Vilsmeier reagent, such as dimethylformamide) at elevated (i.e. increased) temperature, e.g. at a temperature above about 50° C., such as at a temperature from about 65° C. to about 75° C.

As used herein, the term "about" may refer to a value that is ±10% of the value indicated, and may be deleted throughout without altering the general teaching of the invention.

As described herein, we have also found a process for preparing 3-aryl butanals from 3-aryl butenals via highly selective reduction.

Thus, in a second aspect of the invention, there is provided process for the preparation of a compound of formula V

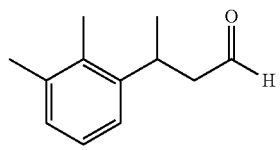

V wherein the process comprises reacting a compound of formula I as defined in the first aspect of the invention with a suitable reducing agent.

In a particular embodiment of the second aspect of the invention, the process comprises the steps of:

(i) providing a compound of formula I using a process as described in the first aspect of the invention; and subsequently (ii) reacting the compound of formula I with a suitable reducing agent to form the compound of formula V.

In a particular embodiment, the suitable reducing agent is a source of hydrogen (i.e. a source of hydrogen atoms) and the reaction is performed in the presence of a suitable catalyst.

In a particular embodiment, the suitable reducing agent is a source of hydrogen (i.e. a source of hydrogen atoms), and the reaction is performed in the presence of one or more (e.g. one) suitable catalyst and one or more (e.g. one) compound suitable for limiting the activity of (i.e. poisoning) said catalyst.

Particular sources of hydrogen that may be mentioned include suitable organic compounds as known to those skilled in the art (such as stable cycloalkyldienes (e.g. cyclohexadiene), hydrazine, dihydronaphthalene, dihydroanthracene, isopropanol, formic acid, methanol or Hantzsch esters, and the like) and hydrogen gas (i.e. molecular hydrogen, $H_2$).

The skilled person will understand that term Hantzsch ester, as used herein, may refer to a compound that, when oxidised, acts as a source of hydrogen. For example, the term may refer to a compound that, when oxidised, acts as a source of hydrogen; for example, following the reaction scheme shown below.

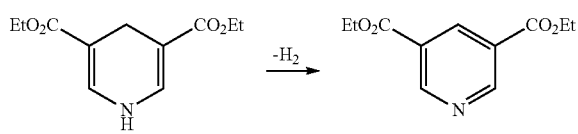 [SMILES: CCOC(=O)C1=CNC=C(C(=O)OCC)C1 ; "-H2" ; CCOC(=O)c1cncc(C(=O)OCC)c1]

The skilled person will understand that the term catalyst, as used herein, refers to a substance that increases the rate of a reaction without modifying the overall standard Gibbs energy change in the reaction.

Particular catalysts that may be mentioned (for example, where the source of hydrogen is hydrogen gas) include metal catalysts, such as palladium (e.g. palladium (Pd) on carbon, for instance 1% Pd on carbon, 2% Pd on carbon, 3% Pd on carbon, 4% Pd on carbon, 5% Pd on carbon, 10% Pd on carbon or 20% Pd on carbon (wherein in each case the % is by weight, i.e. wt %), e.g. 3% Pd on carbon), Raney nickel, Wilkinson's catalyst, Crabtree's catalyst or Lindlar's catalyst. Said catalysts may be present in a homogeneous or heterogeneous reaction mixture. More particular catalysts that may be mentioned include palladium on carbon (e.g. 3% Pd on carbon).

Particular compounds suitable for limiting the activity of (i.e. poisons) of such catalysts (e.g. palladium on charcoal) that may be mentioned include basic salts (such as acetate and carbonate salts, e.g. potassium acetate and potassium carbonate), amines (such as trisubstituted alkyl/aryl amines, e.g. triethanolamine, triethylamine and 4-dimethylaminopyridine (DMAP)), thiols (such as alkyl thiols, e.g. dodecyl mercaptan) and thio urea.

More particular compounds suitable for limiting the activity of (i.e. poisons) of such catalysts (e.g. palladium on charcoal) that may be mentioned include 4-dimethylaminopyridine (DMAP).

Yet more particular compounds suitable for limiting the activity of (i.e. poisons) of such catalysts (e.g. palladium on carbon, such as 3% Pd on carbon) that may be mentioned include a mixture of DMAP and a trisubtituted amine (e.g. a trialkyl amine, such as trimethylamine).

In a particular embodiment of the second aspect of the invention, the process comprises reacting a compound of formula I as defined in the first aspect of the invention with one or more source of hydrogen, one or more suitable catalyst and one or more compound suitable for limiting the activity of said catalyst(s).

In a more particular embodiment of the second aspect of the invention, the process comprises reacting a compound of formula I as defined in the first aspect of the invention with molecular hydrogen (i.e. hydrogen gas), a palladium catalyst (such as palladium on charcoal, e.g. 3% by weight palladium on charcoal) and a compound or mixture of compounds suitable for limiting the activity of said catalyst selected from:
(i) DMAP; and
(ii) a mixture of DMAP and a trialkyl amine, such as triethylamine (e.g. about a 1:4 mixture of DMAP:triethylamine).

In a particular embodiment of the second aspect of the invention, the compound or mixture of compounds suitable for limiting the activity of the catalyst may comprise DMAP, e.g. DMAP in an amount that is 2 to about 8 mol %, such as about 4 to about 6 mol % (e.g. about 5 mol %, such as about 4.8 mol %) relative to the compound of formula I.

The amount and type of the catalyst and, if present, the compound used to poison that catalyst may selected in order to control the selectivity of the reduction reaction and yield of the relevant product. For example:

the catalyst (e.g. 3% Pd on carbon) may be used in an amount that is less than 1 mol % (i.e. % of the molar amount) of the compound of formula I, such as about 0.1 to about 0.9 mol % (e.g. about 0.7 or about 0.3 mol %); and/or the one or more compound used to poison that catalyst may be used in an amount that is less than about 30 mol % of the compound of formula I, which may comprise less than about 10 mol % or, particularly, less than about 6 mol % DMAP, such as about 5 mol % DMAP (e.g. a mixture of about 5 mol % DMAP and about 20 mol % triethylamine relative to the compound of formula I).

The skilled person will understand that, where the suitable reducing agent is hydrogen gas, the process of the second aspect of the invention (i.e. the reduction reaction) may be performed at greater than atmospheric pressure (i.e. of said hydrogen gas), such as at a pressure of greater than about 1.5 bar (e.g. about 1.5 to about 5.5 bar, such as about 2 bar or about 4 to about 5 bar). In such instances, the reaction may be performed in an autoclave.

The skilled person will understand that the temperature at which the reaction is conducted and the duration for which the reaction conditions are maintained may be adjusted to maximise the yield and purity of the required product. For example, the reaction may be conducted at room temperature (i.e. without heating or cooling) and for a period of greater than about 5 h, such about 5 to about 7 h (e.g. about 6 h) or about 20 to about 24 h (e.g. about 22 h).

The skilled person will understand that the process of the second aspect of the invention may be performed in the presence of a suitable solvent, such as toluene, methanol, ethanol, dihydronaphthalene, dihydroanthracene, isopropyl alcohol, isopropyl acetate and/or formic acid. For example, the suitable solvent may be toluene or isopropyl acetate.

The compound of formula V obtained from the process of the second aspect of the invention may be obtained in sufficient purity such that it may be used in subsequent reactions without purification. However, we have found that steps taken to purify the compound of formula V may allow for more convenient storage and increased stability of that compound.

Thus, in a particular embodiment of the second aspect of the invention, the compound of formula V is used in further processes without additional purification (i.e. without additional steps, performed prior to its use in further processes, that are intended to increase the purity of the sample of the compound).

In a more particular embodiment of the second aspect of the invention, the process comprises the further step of isolating and optionally purifying the compound of formula V.

In particular, we have found that the compound of formula V may be purified and stabilised (i.e. for stability during storage) in a highly efficient manner through formation of the corresponding bisulfite adduct.

Thus, in a particular embodiment of the second aspect of the invention, the compound of formula V is isolated as (and/or purified via the formation of) a bisulfite adduct of formula VI

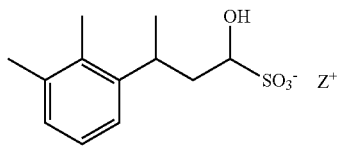

VI wherein Z represents an alkali metal.

Unless otherwise specified, the term alkali metal, when used herein, refers to an element selected from Group I of the periodic table of elements (e.g. sodium, potassium or lithium).

Compounds of formula VI may be novel. Thus, in a third aspect of the invention, there is provided a compound of formula VI as defined herein (i.e. in the second aspect of the invention).

Particular alkali metals that may be mentioned include potassium and, more particularly, sodium. Thus, particular compounds of formula VI that may be mentioned include those where Z represents Na.

In a particular embodiment of the second and third aspects of the invention the compound of formula VI is a compound of formula VIa

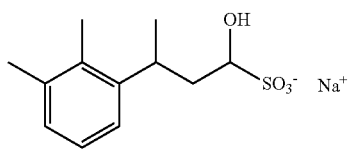

VIa

Compounds of formula VI and VIa may also be depicted in non-ionised forms, which forms will represent the same compounds. For example, the compound of formula VIa may be depicted as follows.

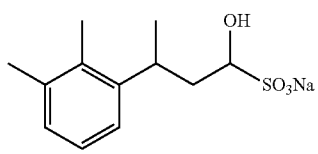

Compounds of formula VI (such as the compound of formula VIa) may be prepared using techniques known to those skilled in the art.

In a fourth aspect of the invention, there is provided a process for preparing a compound of formula VI as defined in the second and third aspects of the invention, wherein the process comprises reacting a compound of formula V as defined in the second aspect of the invention with a compound having the formula $ZHSO_3$, wherein Z is as defined in the corresponding compound of formula VI.

Alternatively, the fourth aspect of the invention may be referred to as a process for purifying (i.e. increasing the purity of said compound; for example, increasing the purity by at least 10%, such as by at least 20% or at least 30%) a compound of formula V.

In a particular embodiment of the fourth aspect of the invention, the compound of formula VI is a compound of formula VIa as defined in the second and third aspects of the invention.

The skilled person will understand that the process of the fourth aspect of the invention may be performed in the presence of a suitable solvent, such as ethanol and/or ethyl acetate.

Compounds of formula VI (such as compounds of formula VIa) may be further purified using techniques known to those skilled in the art, such as recrystallization from a suitable solvent. Thus, in a particular embodiment of the fourth aspect of the invention, the process comprises the further step of recrystallizing the compound of formula VI.

The skilled person will understand that the compounds of formula V may be obtained (i.e. regenerated) from compounds of formula VI through hydrolysis, which may be performed under conditions known to those skilled in the art.

As described herein, 3-aryl butenals and 3-aryl butanals may be useful in the synthesis of the commercially important compound medetomidine.

In a fifth aspect of the invention, there is provided a process for the preparation of compound of formula VII (i.e. medetomidine)

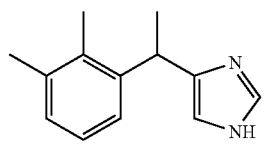

VII or a suitable salt thereof, wherein the process comprises the steps of:
(i) providing a compound of formula I using a process as described in the first aspect of the invention; and/or
(ii) providing a compound of formula V using a process as described in the second aspect of the invention (or, alternatively, by hydrolysis of a compound of formula VI, which compound of formula VI may be prepared using a process as described in the fourth aspect of the invention).

Suitable salts that may be mentioned include pharmaceutically acceptable salts as known to those skilled in the art. More particular salts that may be mentioned include acid-addition salts.

Such acid addition salts may be formed by conventional means, for example by reaction of a free base form of a compound of formula I with one or more equivalents of an appropriate acid, optionally in a solvent or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

Particular acid addition salts that may be mentioned include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate (e.g. D- or L-tartrates and/or derivatives thereof, such as D- or L-tartrate derivatives (e.g. di-p-toluoyl-D-tartaric acid)), phenylacetate, mandelate, phenylpropionate, phenylbutyrate, benzoate, chlorobenzoate, methylbenzoate, hydroxybenzoate, methoxybenzoate, dinitrobenzoate, o-acetoxybenzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g.

hydro chloride, bromide or iodide salts), sulfonate salts (e.g. benzenesulfonate, methyl-, bromo- or chloro-benzenesulfonate, xylenesulfonate, methanesulfonate, ethanesulfonate, propanesulfonate, hydroxyethanesulfonate, 1- or 2-naphthalene-sulfonate or 1,5-naphthalenedisulfonate salts) or sulfate, pyrosulfate, bisulfate, sulfite, bisulfite, phosphate, monohydrogenphosphate, dihydrogenphosphate, metaphosphate, pyrophosphate or nitrate salts, and the like. More particular salts that may be mentioned include the hydrochloride salt.

In a particular embodiment, the process comprises the steps of:

(I) preparing a compound of formula V using a process as described in the second aspect of the invention (including wherein the compound of formula V is prepared from a compound of formula I that is prepared using a process as described in the first aspect of the invention);

(II) reacting the compound of formula V to form a compound of formula VIII

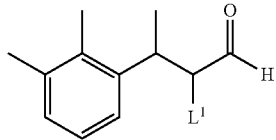

VIII wherein $L^1$ represents a suitable leaving group; and (III) reacting the compound of formula VIII in the presence of (a) a source of formamidine, or (b) formamide, to form the compound of formula VII, or a suitable salt thereof.

In an alternative embodiment, step (I) in the embodiment described directly above many instead require preparation of a compound of formula V by hydrolysis of a compound of formula VI (e.g. a compound of formula VIa), which compound of formula VI may be prepared using a process as described in the fourth aspect of the invention.

In a particular embodiment, $L^1$ represents a halide (such as iodo, chloro or bromo). In a more particular embodiment, $L^1$ represents bromo.

In a particular embodiment, the source of formamidine is formamidine, formamidine acetate, formamidine hydrohalide, formamidinesulfinic acid, or a mixture of ammonium chloride and formic acid.

Compounds of formula V may be reacted to provide compounds of formula VIII, and compounds of formula VIII may be reacted to provide compounds of formula VII, using techniques as described in WO 2013/014428, the entire contents of which are incorporated herein by reference.

In a particular embodiment, where $L^1$ represents bromo, the corresponding bromination may be conducted in the presence of a brominating agent (i.e. any suitable source of bromide ions), such as 5,5-dibromo barbituric acid.

Alternatively, the brominating agent may be bromine (i.e. $Br_2$). For example, the bromination may be performed in the presence of bromine and a suitable solvent, such as isopropyl acetate and, optionally, in the presence of a suitable complexing agent, such as 1,4-dioxane.

The skilled person will understand that the bromination may be performed at a suitable temperature, such as at reduced temperature (for example, at a temperature of from about −15 to about −25° C., or at a temperature of about −10° C.).

In an alternative embodiment, the preparation of compounds of formula VIII may proceed via an intermediate, which intermediate may be a derivative of the compound of formula V. Such intermediates may be formed through the addition of further components to the process, which components may, in particular, be organic compounds and/or catalytic (in respect of the production of compounds of formula VIII).

In particular, the process for preparing compounds of formula VIII from compounds of formula V may be performed in the presence of a compound of formula IX, $$HN(R^x)R^y \qquad\qquad IX$$

wherein:

$R^x$ and $R^y$ both independently represent a $C_{1-6}$ alkyl group optionally substituted with one or more substituents selected from halo, —CN and $C_{1-6}$ alkoxy (wherein the latter group is optionally substituted with one or more fluoro atoms), or $R^x$ and $R^y$ may be taken together to form, together with the nitrogen atom to which they are both attached, a 5- to 7-membered heterocycloalkyl group, optionally containing one or two additional heteroatom-containing groups selected from O, S and $NR^z$, and optionally substituted with one or more substituents selected from halo, —CN, $C_{1-6}$ alkyl and $C_{1-6}$ alkoxy (wherein the latter two groups are optionally substituted with one or more fluoro atoms); and $R^z$ represents H or a $C_{1-6}$ alkyl group, wherein the latter group is optionally substituted with one or more substituents selected from halo, —CN and $C_{1-6}$ alkoxy (wherein the latter group is optionally substituted with one or more fluoro atoms).

As used herein, the term heterocycloalkyl refers to cycloalkyl groups as defined herein but containing at least one heteroatom (in particular, at least one atom selected from O, S and N) as part of a ring. In particular, such groups may be monocyclic.

Particular compounds of formula IX that may be mentioned include those in which $R^x$ and $R^y$ are taken together to form, together with the nitrogen atom to which they are both attached, a 5- to 7-membered (e.g. 6-membered) heterocycloalkyl group optionally containing one or two (e.g. one) additional heteroatom-containing group(s) selected from O, S and $NR^z$ (e.g. one O atom).

More particular compounds of formula IX that may be mentioned include morpholine.

Where the process for preparing compounds of formula VIII from compounds of formula VIa involves the addition of a compound of formula IX, the skilled person will appreciate that the reaction may proceed via a compound of formula X

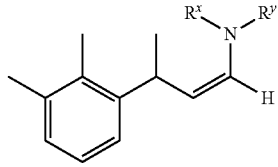

X wherein $R^x$ and $R^y$ are as defined herein in respect of compounds of formula X.

Compounds of formula VIII may be prepared from compounds of formula X using techniques as known to those skilled in the art, such as under conditions as herein described in respect of the preparation of compounds of formula VIII from compounds of formula V.

Particular compounds of formula X that may be mentioned include compounds of formula Xa

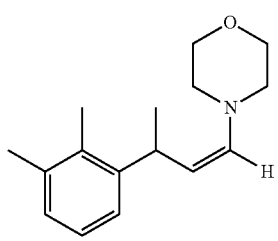

In particular, where the process involves the addition of a compound of formula IX and/or proceeds via (or starting from) a compound of formula X (e.g. a compound of formula Xa), the reaction may first involve addition of a compound of formula IX (e.g. morpholine) to a compound of formula V in the presence of a suitable solvent and, optionally, under conditions suitable for the removal of water from the reaction mixture (for example, wherein the solvent is toluene and, following addition of the compound of formula IX, the reaction is heated to the reflux point of the solvent under so-called Dean-Stark conditions (i.e. using a Dean-Stark distillation apparatus)).

More particularly, the process may involve addition of an excess (i.e. greater than one equivalent) of the compound of formula IX relative to the compound of formula V, such as about 1.1 to about 2 equivalents (e.g. about 1.5 equivalents).

Alternatively, certain compounds of formula IX (such as morpholine) may also be used as the suitable solvent (e.g. where the reaction is performed under conditions suitable for the removal of water from the reaction mixture, such as under Dean-Stark conditions).

For the process for the conversion of a compound of formula V to the compound of formula VIII (in particular, where the process does not involve the addition of a compound of formula IX and/or proceed via a compound of formula X), the compound of formula V may be reacted in the presence of 5,5-dibromo barbituric acid, for instance such that there is at least one equivalent of bromide ions in the reagent employed (e.g. where the reagent provides two equivalents of the halide ion, then about 0.5 equivalents, compared to the compound of formula V, may be employed). The compound of formula V may first be dissolved in an appropriate solvent (e.g. a polar aprotic solvent such as an ether, especially tetrahydrofuran (THF)) and a small molar equivalent (i.e. a sub-stoichiometric amount) of HCl (e.g. 37% HCl) may be added. This mixture may first be heated (e.g. to above 40° C., such as about 60° C. or up to the boiling point of the solvent), after which the appropriate brominating agent (e.g. 5,5-dibromo barbituric acid) may be added. In particular, it may be added in portions such that the temperature (when the reaction is performed in e.g. THF) is kept below the boiling point (i.e. below about 65° C.). The desired product may be isolated by a work up procedure, e.g. as described in the examples hereinafter.

Alternatively, for the process for the conversion of the compound of formula V to the compound of formula VIII (in particular, where the process involves the addition of a compound of formula IX and/or proceeds via (or starting from) a compound of formula X), the reaction may be performed in the presence of bromine (i.e. $Br_2$) and, optionally, a suitable solvent (such as ethyl acetate). In particular, such reactions may be performed in the presence of least one equivalent of bromine (i.e. one equivalent of $Br_2$) relative to the compound of formula V (or the compound of formula X), such as a slight excess of bromine (e.g. about 1.01 to about 1.05 equivalents, such as about 1.04 equivalents).

In a particular embodiment of the fifth aspect of the invention, the reaction of the compound of formula VIII to form the compound of formula VII (i.e. step (III) in the embodiment described above) may be performed in the presence of a source of formamidine (e.g. formamidine, or an appropriate salt or derivative thereof). More particularly, it may be performed in the presence of formamidine acetate, although other derivatives are also possible, for instance other salts such as formamidine hydrohalide (e.g. HCl), formamidinesulfinic acid and/or other salts or derivatives that may be commercially available). The use of formamidine and, in particular, formamidine acetate may have the advantage that the process of the invention is improved, e.g. in terms of yield and purity.

In a more particular embodiment, the step (III) is performed in the presence of formamidine acetate.

In particular, at least one equivalent of the reagent that promotes the imidazole ring-forming reaction (e.g. formamidine acetate) is employed compared to the compound of formula VIII, such as from about 1.1 to about 2.5 equivalents, for instance about 1.5 equivalents or about 2 equivalents.

In particular, the reaction of the compound of formula VIII to form the compound of formula VII may be performed in the presence of a suitable solvent, such as a polar organic solvent, for instance an alcohol solvent. Particular solvents that may be mentioned are ethanol and IPA. The quantity of solvent, relative to the compound of formula VIII should be sufficient for the reaction to proceed efficiently. For instance, at least a 1:1 ratio of compound of formula VIII:alcoholic solvent (by weight) is employed, such as a ratio of at least 1:2, such as at least 1:3. Although the ratio may be 1:10, particular ratios that may be mentioned are from 1:4 to 1:6 (e.g. between 1:4 and 1:6, such as about 1:5). More particularly, the ratio may be from 1:6 to 1:7 (e.g. between 1:6 and 1:7, such as about 1:7). Higher quantities of solvent have the disadvantage that the reaction rate may decrease due to the higher dilution and additionally may have environment/economical disadvantages. In particular, the suitable solvent may be selected from ethanol, iso-propyl alcohol (IPA), or a mixture of ethanol or iso-propyl alcohol and water (such as an approximately equal mixture) (e.g. iso-propyl alcohol (IPA)); for example, a ratio of 1:7 of compound of formula VIII:IPA (by weight) may be employed.

Additionally, the reaction of the compound of formula VIII to form the compound of formula VII may be performed in the presence of a non-aqueous ionising solvent (in addition to the solvent that may already be present (e.g. the alcoholic solvent)). In this respect, particular additional solvents that may be mentioned are liquid or aqueous ammonia (for instance, 25% aqueous ammonia may be employed). Compared to the compound of formula VIII, at least 1 molar equivalent of the non-aqueous solvent is employed (e.g. at least 5 molar equivalents, such as from 5 to 20 molar equivalents (e.g. between 5 and 20 molar equivalents), preferably about 10 molar equivalents). In terms of relative weights, compared to the primary solvent employed (e.g. the alcoholic solvent such as IPA), assuming the additional solvent is 25% aqueous ammonia, the ratio of primary solvent to additional solvent is from 1:2 to 10:1 (e.g. between 1:2 and 10:1), particularly from 1:1 to 5:1 (e.g. between 1:1 and 5:1, such as about t5:1 or 2:1).

In particular, the non-aqueous solvent may be liquid ammonia; for example, compared to the compound of formula VIII, from 5 to 20 molar equivalents of liquid ammonia may be used (particularly from about 6 to about 16, such as from about 8 to about 15 (e.g. about 9 (such as about 8.9), about 12 or 13 (such as about 12.5) or about 14 (such as about 14.4) molar equivalents of liquid ammonia compared to the compound of formula VIII).

In a particular embodiment of the fifth aspect of the invention, the primary solvent used in step (III) (i.e. in the embodiment described above) is IPA and the non-aqueous ionising solvent is liquid ammonia (i.e. the solvent used in the reaction is a mixture of IPA and liquid ammonia); for example, the reaction may be performed in solvent at least 90% (e.g. at least 95%, such as at least 99%) of which consists of a mixture of IPA and liquid ammonia. More particularly, in terms of relative weights, the ratio of IPA to liquid ammonia may be from 6:1 to 12:1, such as from about 8:1 to about 11:1 (e.g. about 11:1 or about 86:10); for example, the reaction may be performed in solvent mixture which is from 6 to 12% by weight of liquid ammonia in IPA (e.g. about 8.3% by weight or, particularly, about 10.4% by weight of liquid ammonia in IPA).

In a particular embodiment of the fifth aspect of the invention, step (III) (i.e. in the embodiment described above) may be performed at elevated temperature, e.g. at above room temperature (e.g. at above 50° C., such as above 80° C., for instance at about 120° C., depending on the boiling point of the solvent system that is employed) for a period of time (e.g. about 2 hours) although the temperature and reaction time may be varied in order to maximise reaction efficiency and yield. For example, where the solvent is a mixture of liquid ammonia and IPA (e.g. 10.4% by weight of liquid ammonia in IPA), the reaction may be performed at a temperature of from about 70 to about 90° C. (such as from about 75 to about 85° C., e.g. from about 77 to about 83° C.). More particularly, the reaction may comprise the step of adding the compound of formula VIII to a preheated mixture comprising:
(a) some or all of the required solvent(s) (e.g. the mixture of IPA and liquid ammonia; for example, a mixture comprising at least 50% of the total solvent(s) used in the reaction); and
(b) the source of formamidine, such as formamidine (or a salt or derivative thereof, such as formamidine acetate, formamidine hydrohalide and/or formamidinesulfinic acid) or a mixture of an ammonium salt (e.g. an ammonium halide, such as ammonium chloride) and formic acid.

As used herein, the term preheated will be understood as referring to a mixture that, at the point of addition of the compound of formula VIII, is at elevated temperature, for example at above room temperature (for instance at above about 50° C., such as above about 70° C. (e.g. from about 70° C. to about 120° C.), depending on the boiling point of the solvent system that is employed and the particular pressure that the reaction is performed at). For example, where the solvent is a mixture of liquid ammonia and IPA (e.g. 10.4% by weight of liquid ammonia in IPA), the preheated mixture may be at a temperature of from about 70° C. to about 90° C. (such as from about 75° C. to about 85° C., e.g. from about 77° C. to about 83° C.).

In a more particular embodiment, the reaction may be performed in a sealed container and, optionally, at elevated pressure (i.e. at greater than atmospheric pressure). In particular, the process may be performed in a sealed container and at elevated temperature and/or elevated pressure (e.g. wherein the container is sealed and then the contents heated to elevated temperature, thus resulting in the reaction being performed at elevated pressure).

In more particular embodiments of the fifth aspect of the invention, one or more of the following statements may apply to step (III) as described in the embodiment above.
(a) The reaction is performed in the presence of formamidine acetate.
(b) The reaction is performed in a solvent which is a mixture of IPA liquid ammonia, such as a 6 to 12% by weight of mixture of liquid ammonia in IPA (e.g. about 8.3% by weight or, particularly, about 10.4% by weight of liquid ammonia in IPA).
(c) The reaction is performed at a temperature of from about 70 to about 90° C. (such as from about 75 to about 85° C., e.g. from about 77 to about 83° C.).
(d) The reaction includes the step of adding the compound of formula VIII to a preheated mixture of the solvent(s) and the formamidine (or a salt or derivative thereof), ammonium chloride/formic acid or the like, wherein the preheated mixture may be at a temperature of from about 70 to about 90° C. (such as from about 75 to about 85° C., e.g. from about 77 to about 83° C.).
(e) The reaction is performed in a sealed container and, optionally, at elevated pressure.

In a particular embodiment that may be mentioned, each of statements (b) to (e) above apply. In a more particular embodiment, each of statements (a) to (e) above apply.

As described herein, the skilled person will appreciate that the process of the fifth aspect of the invention (including any one or more embodiment thereof) may further comprise the step of reacting the compound of formula VII to form the corresponding salt (e.g. the hydrochloride salt) using techniques known to those skilled in the art.

In a particular embodiment of the fifth aspect of the invention, the process comprises the further step of isolating and optionally purifying the compound of formula VII, or suitable salt thereof.

The product of formula VII may be isolated after the process of the fifth aspect of the invention using techniques known to those skilled in the art. For instance the solvent system (e.g. ammonia and IPA) may be removed (e.g. preferably at normal atmospheric pressure, for instance by boiling the solvent; although the solvent system may also be removed under reduced pressure, e.g. by distillation at reduced pressure) to leave a residue. The residue may be taken up in a mixture of water and organic solvent, or, in another embodiment, the residue may be added to water (in the latter embodiment, the crude product can simply be separated from the water layer, circumventing the need to employ organic solvent in that step). When the residue is taken up in a mixture of water and organic solvent, then the organic solvent may be any non-water soluble organic solvent that dissolves the product (e.g. a polar organic solvent such as ethyl acetate, or a non-polar organic solvent such as an aromatic solvent, e.g. toluene). In this case, the pH of the mixture (the residue, water and organic solvent) may be adjusted to 9-10 (by employing e.g. a carbonate base, hydroxide base, alkoxide base or the like, e.g. sodium carbonate or sodium hydroxide) and the phases separated. The organic phase may then be washed with dilute hydrochloride acid so that the product is substantially in the aqueous phase. After the organic phase is separated, the pH of the aqueous phase (containing the product) may then be adjusted to pH 9-10 (by employing e.g. a carbonate base, hydroxide base, alkoxide base or the like, e.g. sodium carbonate or sodium hydroxide) and the product extracted again with organic solvent (e.g. a polar organic solvent, such as ethyl acetate, or a non-polar organic solvent such as an aromatic solvent, e.g. toluene). The water phase is separated and the organic phase concentrated to leave a residue containing the desired product.

The product of formula VII may be isolated after the process of the fifth aspect of the invention as the free base. For example, the free base may be isolated as a solid (e.g. a crystalline solid), which may obtained via crystallisation from a suitable solvent (such as the organic solvent used in the extraction of the product). Alternatively, the desired product of the compound of formula VII may be isolated from the residue from the work up as a corresponding salt (e.g. the corresponding acid salt, e.g. the HCl salt), for instance by precipitation. Advantageously, the salt (e.g. HCl salt) of the compound of formula VII may be solid (or even crystalline) and may therefore be easily isolated, for instance the residue may be taken up in an organic solvent (e.g. a polar aprotic organic solvent, such as acetone) and the precipitation of e.g. the hydrogen halide salt may be promoted by the addition of the hydrogen halide (e.g. hydrochloric acid, which may be concentrated, e.g. 37% HCl, or, gaseous HCl may be employed) to a lower pH (e.g. down to about pH 6).

The product may be filtered and washed with more solvent (e.g. acetone). If desired, further product or a second crop of product (e.g. the HCl salt of the compound of formula VII) may be isolated by the distillation of the solvent from the mother liquor followed by the addition of water free acetone. However, when gaseous HCl is employed in the hydrogen halide salt forming step, the isolation of a second crop of product (e.g. the HCl salt thereof) need not be performed.

If the product of formula VII is isolated as the salt, the salt may then be converted to the free base by neutralising the salt. Reaction conditions that may be employed may be described in the examples (e.g. first the salt is dissolved in water and then treated with charcoal), for instance, the neutralisation may be performed by the addition of base (e.g. a hydroxide such as sodium hydroxide), e.g. at elevated temperature (e.g. about 55-60° C.) after which the resulting emulsion may be cooled, e.g. to about 40° C., and crystallisation may be induced by seeding and the free base may thereafter be isolated.

The processes described herein may be operated as a batch process or operated as a continuous (i.e. flow) process, and may be conducted on any scale.

Unless otherwise indicated, the processes described herein may be performed with or without separation (e.g. isolation and/or purification) of any stable intermediate products.

It will be appreciated by those skilled in the art that, in the processes described herein, functional groups of intermediate compounds may be, or may need to be, protected by protecting groups. The protection and deprotection of functional groups may take place before or after any of the reaction steps described herein.

Protecting groups may be removed in accordance with techniques which are well known to those skilled in the art. For example, the use of protecting groups is described in "Protective Groups in Organic Chemistry", edited by J. W. F. McOmie, Plenum Press (1973), and "Protective Groups in Organic Synthesis", 3$^{rd}$ edition, T. W. Greene & P. G. M. Wutz, Wiley-Interscience (1999).

Unless otherwise indicated, starting material and reagents used in processes described herein may be commercially-available and/or may themselves be synthesised from commercially-available starting materials using techniques known those skilled in the art.

In particular, compounds of formula II may be prepared using commercially-available starting materials and using techniques known to those skilled in the art. Compounds of formula II may be prepared by reaction of a compound of XI

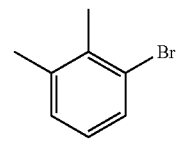

to form an intermediate (Grignard reagent) of formula XII

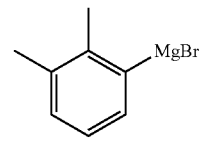

followed by reaction of the compound of formula XII with acetone to form the compound of formula II, using techniques and conditions known to those skilled in the art.

Compounds employed in or produced by the processes described herein (i.e. those involving the process of the invention) may exhibit tautomerism. The process of the invention therefore encompasses the use or production of such compounds in any of their tautomeric forms, or in mixtures of any such forms.

Similarly, the compounds employed in or produced by the processes described herein (i.e. those involving the process of the invention) may also contain one or more asymmetric carbon atoms and may therefore exist as enantiomers or diastereoisomers, and may exhibit optical activity. The process of the invention thus encompasses the use or production of such compounds in any of their optical or diastereoisomeric forms, or in mixtures (e.g. racemic mixtures) of any such forms.

Particular compounds of formulas V, VI (including VIa), VII, VIII and X as described herein that may be mentioned include the S enantiomers of those compounds. For example, the compound of formula VII as described herein may be provided in the form of the S enantiomer, as depicted below, which may be referred to as dexmedetomidine.

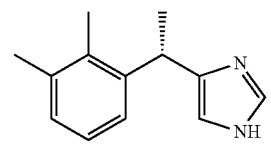

Further, the compounds employed in or produced by the processes described herein may contain double bonds and may thus exist as E (entgegen) and Z (zusammen) geometric isomers about each individual double bond. All such isomers and mixtures thereof are included within the scope of the invention.

The processes described herein may be performed employing salts, solvates or protected derivatives, thereby producing compounds that may or may not be produced in the form of a corresponding salt or solvate, or a protected derivative thereof. In particular, the processes described herein may produce compounds that are in the form of the corresponding salt (e.g. the hydrochloride salt), wherein said processes may further comprise the step of reacting the product to form the corresponding salt using techniques known to those skilled in the art.

Processes of the invention may have the advantage that they are, inter alia, more efficient (e.g. higher yielding), use less energy, use less toxic reagents, produce fewer by-products and/or are cheaper to run than processes described in the prior art. In particular, processes as described herein (such as the process of the first aspect of the invention) may have the advantage that they are more suitable for use in large-scale industrial manufacture than processes described in the prior art.

EXAMPLES

The following examples are merely illustrative examples of the processes of the invention described herein. All equipment, reagents and solvents used were standard laboratory equipment, e.g. glassware, heating apparatus and HPLC apparatus.

Example 1

Preparation of tertiary alcohol
(2-(2,3-xylyl)-2-propanol)

2,3-Dimethylbromobenzene (150 g, 0.80 mol) was dissolved in THF (250 mL). To Mg-turnings (20.5 g, 0.84 mol) in THF (300 mL) was added 90 mL of 2,3-dimethylbromobenzene solution prepared above. The solution was warmed to 50° C. and 1,2-dibromoethane (1 mL) was added to initiate the reaction. The rest of 2,3-dimethylbromobenzene solution was added over 50 minutes at 64-65° C. The mixture was refluxed for 1 h and then 300 mL of THF was distilled off at atmospheric pressure.

The mixture was cooled to 50° C. and toluene (500 mL) was added followed by cooling to room temperature. Then the solution of acetone (61 g, 1.05 mol) in toluene (100 mL) was added over 1 h at 24-29° C. The obtained slurry was stirred for 13 h at room temperature.

The slurry was cooled to 12° C. neutralized with aqueous HCl at 13-15° C. The lower aqueous phase was cut off and the organics washed with 5% NaHCO₃ (250 mL) and water (250 mL).

The solvents were removed at 40-50° C. and at 50-100 nnbar. Then, heptane (150 mL) was added and the solution was cooled to minus 10° C. The solids were filtered and washed with cold heptane (100 mL) to obtain wet crop-1 (74.4 g) that after drying in vacuo gave 73.6 g (55.8% from theory) of dry 2-(2,3-xylyl)-2-propanol, determined to be pure by $^1$H NMR.

The filtrate was concentrated to 52.5 g residue. Dilution with heptane (50 mL), crystallization on cooling, filtration, washing with heptane and drying gave 2-(2,3-xylyl)-2-propanol (crop 2, 16.8 g, 12.7% from theory) of product. Overall yield 68.5% from 2,3-dimethylbromobenzene.

Example 2

Preparation of unsaturated aldehyde
(3-(2,3-xylyl)-2-butenal)

The tertiary alcohol 2-(2,3-xylyl)-2-propanol (8.83 g, 0.054 mol) was dissolved in DMF (12 mL, 0.16 mol) and the solution was cooled to 1° C. POCl₃ (12.5 mL, 0.13 mol) was then added at <13° C. (exothermic reaction) in 50 minutes. The mixture was heated to 75-85° C. and reacted for 2 h, then cooled to room temperature and poured into ice-water. The mixture was neutralized with 4M NaOH, extracted with MTBE and the organic extract was washed with water.

Removal of the solvent left 9.06 g of 3-(2,3-xylyl)-2-butenal as an oil with 92% assay by NMR (sum of E- and Z-isomers). Yield corrected to assay 89%.

Example 3

Preparation of saturated aldehyde
(3-(2,3-xylyl)-butanal)

An autoclave was charged with 330 g of 12.5% solution of 3-(2,3-dimethylphenyl)but-2-enal in isopropyl acetate (mixture of E and Z isomers; 0.24 mol). 4-(Dimethylamino)pyridine (1.4 g; 12 mmol; 5 mol %) and catalyst (3% Pd/C; 12.0 g; 1.7 mmol; 0.7 mol %) were added. Hydrogenation was carried out at 2 bar and at room temperature for 6 h. GC analysis of the reaction mixture (area %) showed: 84.9% of 3-(2,3-dimethylphenyl)butanal; 0.5% of 3-(2,3-dimethylphenyl)but-2-enol; 0.1% of 3-(2,3-dimethylphenyl)butanol; 6.8% of starting aldehyde.

Example 4

Preparation of saturated aldehyde
(3-(2,3-xylyl)-butanal)

Autoclave was charged with 20.0 g 22% solution of 3-(2,3-dimethylphenyl)but-2-enal in toluene (mixture of E and Z isomers; 25.3 mmol). Charcoal (1.5 g) was added. The mixture was stirred for 1 h. 4-(Dimethylamino)pyridine (0.15 g; 1.23 mmol; 4.8 mol %) and triethylamine (0.50 g; 5 mmol; 19.7 mol %) were added. Catalyst (3% Pd/C; 0.55 g; 0.077 mmol; 0.30 mol %) was added. Hydrogenation was carried out at 4-5 bar and at room temperature for 22 h. Catalyst was filtered off and washed with toluene. After evaporation of solvent 26.4 g of yellow clear liquid was obtained. GC area% showed: 96.9% of 3-(2,3-dimethylphenyl)butanal; 0.6% of 3-(2,3-dimethylphenyl)but-2-enol; 0.3% of 3-(2,3-dimethylphenyl)butanol; 0.9% of starting aldehyde. NMR assay 15%; yield 89%.

Example 5

Preparation of bromo aldehyde (3-(2,3-xylyl)-2-bromo-butanal) (1)

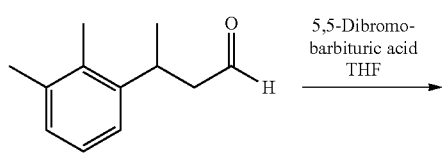

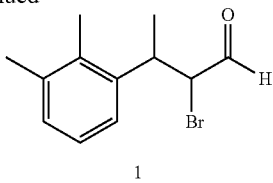

3-(2,3-xylyl)-butanal, 945.8 g, 5.37 mol, is dissolved in 3880 g THF. 37% Hydrochloric acid, 31.2 g, 0.32 mol, is added and the mixture heated to 60° C. 5,5-Dibromobarbituric acid, 767.6 g, 2.69 mol, is added in portions keeping the temperature below 65° C. The mixture is then stirred for 30 minutes at 60-65° C. THF is stripped under reduced pressure followed by the addition of 2980 g toluene. Residual THF is then distilled under reduced pressure. The toluene phase is washed with 3×3.2L water followed by 1.6L 3% aqueous triethanolamine and finally with 1.6L water. To the toluene phase is added 200 mg triethanolamine and 200 mg BHT. The toluene is stripped at reduced pressure leaving 1150 g, 4.51 mol, 84%, of 3-(2,3-xylyl)-2-bromo-butanal (1).

Example 6

Synthesis of Medetomidine

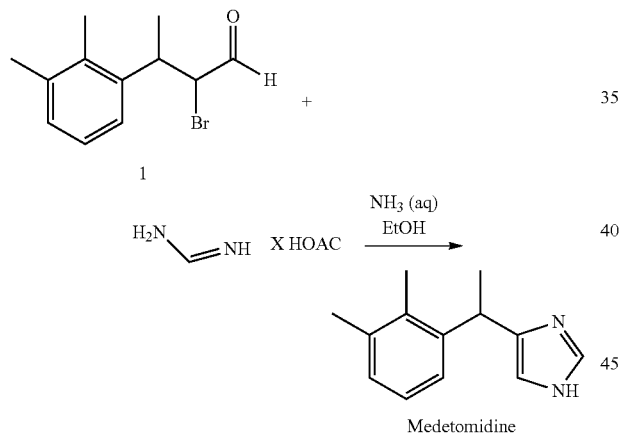

To a SS pressure reactor is added 3-(2,3-xylyl)-2-bromo-butanal (1), 1154 g, 4.53 mol, formamidine acetate, 939 g, 9.02 mol, ethanol, 5280 g and finally 25% aqueous ammonia, 3050 g, 44.9 mol. The mixture is heated at 120° C. for 2 h. Ethanol and ammonia is stripped at atmospheric pressure and the residue dissolved in 1200 ml water and 700 ml ethyl acetate. The pH is adjusted to 9-10 with sodium carbonate and the water phase separated. The product is extracted to water by three successive washes with diluted hydrochloric acid. The pH of the acidic aqueous phase is adjusted to 9-10 with sodium carbonate and the product extracted to 500 ml ethyl acetate. The water phase is separated and the ethyl acetate removed at reduced pressure. The residual oil is dissolved in acetone, 4L, and the product precipitated as the HCl salt by addition of 37% hydrochloric acid to pH 6. Filtration and washing with acetone gives 366 g of Medetomidine×HCl. A second crop of product, 96 g, was isolated by distilling the solvent from the mother liquor followed by the addition of water free acetone. In total, 462 g, 1.95 mol, 43%, of pure Medetomidine×HCl was isolated.

Medetomidine×HCl, 783 g, 3.31 mol, is dissolved in 2.5L water. Charcoal, 40 g, is added and the mixture stirred for 30 minutes at 70° C. The charcoal is filtered and washed with 0.5L water. The combined filtrate and washing is diluted with 3.1L acetone and 0.2L water. The temperature is adjusted to 55-60° C. and a solution of 132 g, 3.3 mol, sodium hydroxide in 0.54L water is added over ca 1 h. The resulting emulsion is cooled to ca 40° C. and crystallization is induced by seeding. The slurry is cooled to 0° C., filtered and the filter cake washed with 3×400 ml water. Drying under vacuum afforded 590 g, 2.95 mol, 89%, of Medetomidine free base.

Example 7

Preparation of bromo aldehyde (3-(2,3-xylyl)-2-bromo-butanal)

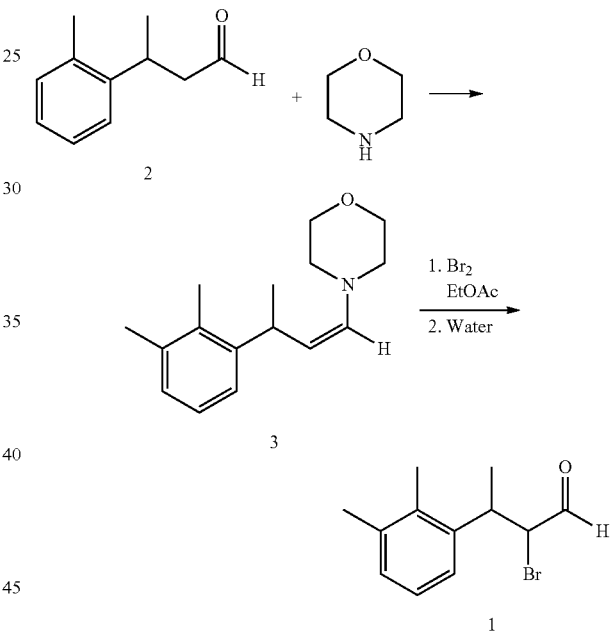

To 3-(2,3-dimethylphenyl)butanal (2) in toluene (82.2 g, 0.28 mol) is added toluene (93 mL) and morpholine (36 mL, 0.42 mol). The mixture is heated to reflux with a Dean-Stark trap mounted in order to remove formed water. When the theoretical amount of water have been removed and no more water is distilled off solvents is distilled off until reaching a residual volume of 110 mL. The resulting enamine intermediate (3) was used directly.

To a second reaction vessel is added bromine (15 mL, 0.29 mol) and ethyl acetate (566 mL) and the mixture is cooled below −10° C. To this bromine solution is added the enamine solution prepared above in a rate keeping the temperature below −10° C. After at least 10 minutes of stirring water (185mL) is added to quench the reaction and then the temperature is increased to 25° C. If necessary the pH is adjusted to below 4 by adding hydrochloric acid. The stirring is stopped and the phases are allowed to separate during 10 minutes. The lower phase is discarded. A solution of sodium bicarbonate (7.6 g) and sodium thiosulfate 7.5 g)

in water (132 mL) is added and the mixture is stirred for 10 minutes and then the phases are allowed to separate during 10 minutes. The lower phase is discarded. Water (153 mL) is added and the mixture is stirred for 10 minutes before stirring as stopped and the phases are allowed to separate. The lower phase is discarded. BHT (0.1 g) and triethanolamine (0.1 g) is charged. Solvents are distilled of with applied vacuum until a residual volume of 93 mL. The crude product solution containing 62.8 g 2-bromo-3-(2,3-dimethylphenyl)butanal (1) is collected. Overall yield from 1-Bromo-2,3-dimethylbenzene is 61%.

Examples 8(a) to (d)

Preparation of Medetomidine

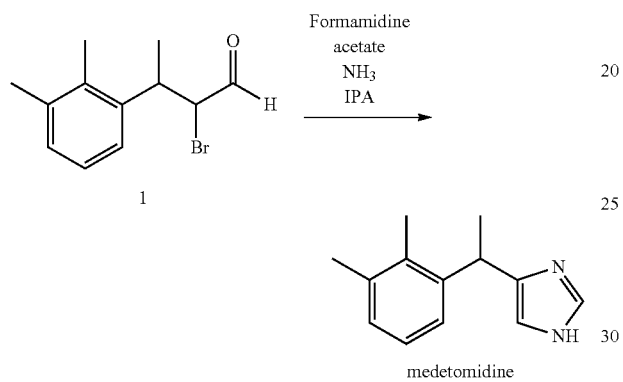

Example 8(a)

The reaction was performed in a PTFE-lined bomb. The bromoaldehyde (3.4 g; containing 2.5 g, 9.8 mmoles of bromoaldehyde by NMR assay) and 2.04 g (19.6 mmoles) formamidine acetate were mixed with 30 mL isopropanol containing ammonia (8.3%; 118 mmoles). The mixture was heated on oil-bath at 77-80° C. for 2 h. After cooling to 21° C. GC analysis showed 74.8 area % of Medetomidine and about 11-12% high boiling by-products (including pyrazines).

The reaction mixture was concentrated on rotavapor. To the residue (10.7 g) 15 mL of toluene, 15 mL of water and 1 mL of 30% sodium hydroxide were added. The mixture was warmed to 30° C. and the phases were separated. Lower water phase (pH-11-12) was discarded. Toluene phase was assayed by NMR to give 70% yield of medetomidine.

Example 8(b)

Formamidine acetate (0.25 g) was mixed with 3 mL 10.4% w/w ammonia solution in 2-propanol. The mixture was immersed into oil bath (77° C.). Formamidine acetate dissolved at about 70° C. resulting in colorless solution.

The bromoaldehyde (sample weight 0.42 g, calculated to contain 0.31 g of bromoaldehyde) was added with micro syringe during 20 min at 77-80° C. Stirring was continued at 76-81° C. bath temperature for 2 h.

GC analysis of crude product showed 84.5% medetomidine and 3.7% of high-boiling by-products.

Example 8(c)

Formamidine acetate (28.5 g; 0.27 mol) was mixed with 10.4% solution of ammonia in 2-propanol (260 mL; 1.24 mol $NH_3$). Mixture was heated to 83° C. (oil-bath 97° C.). The bromoaldehyde (51 g, 0.137 mol) was pumped into the reactor in 42 minutes. Post reaction at 90-91° C. for 2 h.

Reactor was cooled to RT. The mixture contained 80% medetomidine and 3.2% by-products by GC area% analysis.

Reaction mixture (305.5 g) was concentrated to 112.8 g. To the concentrate 150 mL toluene, 100 mL water and 18 mL 30% NaOH were added. The mixture stirred at 50-55° C. for 10 min and phases were separated. Toluene phase was assayed by NMR to give 81% yield of medetomidine.

Example 8(d)

Formamidine acetate (21 g; 0.20 mol) was mixed with 10.4% solution of ammonia in 2-propanol (250 mL; 1.2 mol of $NH_3$). Mixture was heated in oil-bath to 80° C. (oil-bath 97° C.). The bromoaldehyde (50 g; 0.134 mol) was pumped into the reactor in 40 minutes at 85-89° C. After 2 h post reaction the mixture was cooled to RT. The mixture contained 80% medetomidine and 3.2% by-products by GC area% analysis.

Isolation was carried out as described in Example 8(c) (directly above).

Toluene phase was assayed by NMR to give 82.8% yield of Medetomidine.

Example 9

Preparation of unsaturated aldehyde (3-(2,3-xylyl)-2-butenal)

Crude 2-(2,3-xylyl)-2-propanol (77.8 g, 74.1% assay, 0.352 mol) was dissolved in DMF (66 mL, 0.856 mol). Then, $POCl_3$ (139 g, 907 mmol) was added over 4.5 hours at temperature not exceeding 75° C. (exothermic reaction). The mixture was reacted at about 70° C. for 4.5 hours. During that period a further 3 mL of $POCl_3$ was added. The mixture was cooled to room temperature and poured into water at 0-5° C. The mixture was neutralized with 25% NaOH, extracted with toluene and the organic extract was washed with water.

The organic phase (194.5 g) had 28.6% assay of 3-(2,3-xylyl)-2-butenal as sum of E- and Z-isomers. Yield corrected to assay was 91%.

Example 10

The products mentioned herein, e.g. obtained by the procedures disclosed herein (such as those listed in Examples 8(a) to (d) above), may be formulated into a suitable end-product, e.g. in the case of the synthesis of the final product medetomidine into an antifouling agent such as Selektope™ using standard formulation techniques. For instance, medetomidine free base may be dissolved in an organic solvent to prepare the final formulated product.

Alternatively, medetomidine (e.g. dexmedetomidine), or a pharmaceutically acceptable salt thereof, may be combined with one or more pharmaceutically acceptable excipients in order to provide a pharmaceutical formulation. Such pharmaceutically acceptable excipients will be well-known to those skilled in the art.

ABBREVIATIONS

Abbreviations used herein will be well-known to those skilled in the art. For example, the following abbreviations may have meanings as indicated herein below.

BHT butylated hydroxytoluene
C Celsius
DMAP 4-(dimethylamino)pyridine
DMF dimethylformamide
eq equivalent(s)
h hour(s)
HPLC high-performance liquid chromatography
IPA isopropyl alcohol
MTBE methyl-tert-butyl ether
NMR nuclear magnetic resonance
PTFE polytetrafluoroethylene
THF tetrahydrofuran

The invention claimed is:

1. A process for preparing a compound of formula I

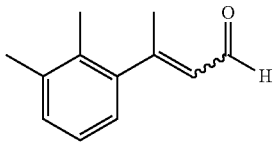

I wherein said process comprises reacting a compound of formula II

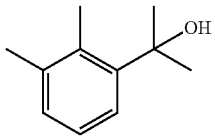

II with one or more suitable Vilsmeier reagent.

2. A process of claim 1, wherein the Vilsmeier reagent comprises a compound of formula IIIa and/or a compound of formula IIIb

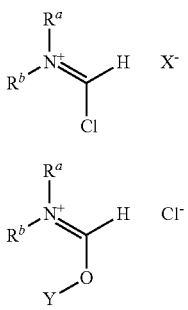

IIIa

IIIb wherein:
X represents counter ion derived from reaction with an acid chloride;
Y represent a substituent derived from reaction with an acid chloride;
each $R^a$ and $R^b$ independently represents H, $C_{1-3}$ alkyl or phenyl, or $R^a$ and $R^b$ taken together with the nitrogen to which they are attached form a pyrollidine, piperidine, morpholine or indoline moiety.

3. A process of claim 1, wherein the Vilsmeier reagent is formed by reaction of dimethylformamide and $POCl_3$, and optionally wherein dimethylformamide also acts as a solvent.

4. A process of claim 1, wherein the process comprises the steps of:
(i) reacting the compound of formula II to form the compound of formula IV

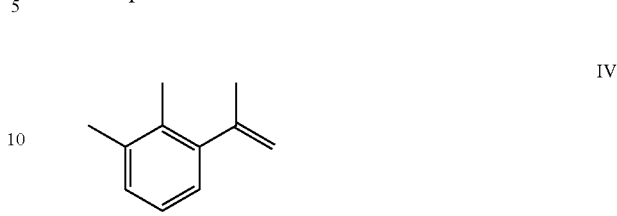

IV and subsequently
(ii) reacting the compound of formula IV to form the compound of formula I.

5. A process of claim 1, wherein the process is performed as a one-pot process and/or without isolation of a compound of formula IV.

6. A process of claim 1, further comprising isolating and optionally purifying the compound of formula I.

7. A process for preparing a compound of formula V

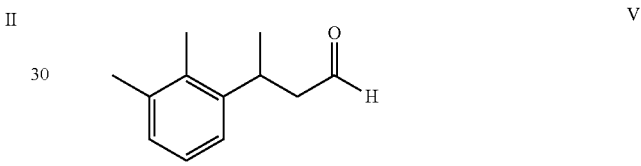

V wherein the process comprises reacting a compound of formula I of claim 1 with a suitable reducing agent.

8. A process of claim 7, wherein the process comprises the steps of:
(i) providing a compound of formula I by reacting a compound of formula II

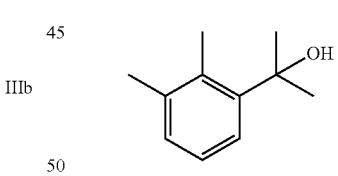

II with one or more suitable Vilsmeier reagent; and subsequently
(ii) reacting the compound of formula I with a suitable reducing agent to form the compound of formula V.

9. A process of claim 7, wherein the suitable reducing agent is a source of hydrogen and the reaction is performed in the presence of one or more suitable catalyst, and optionally performed in the presence of one or more compound suitable for limiting the activity of said catalyst.

10. A process of claim 7, further comprising isolating and optionally purifying the compound of formula V.

11. A process of claim 7, wherein the compound of formula V is isolated as and/or purified via formation of a bisulfite adduct of formula VI

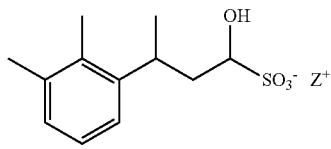

VI wherein Z represents an alkali metal.

12. A compound of formula VI of claim 11.
13. A process for preparing a compound of formula VI

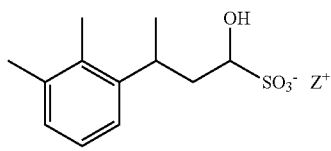

VI wherein Z represents an alkali metal; comprising reacting a compound of formula V of claim 7 with a compound having formula ZHSO₃, wherein Z represents an alkali metal.

14. A process of claim 11, wherein Z represents Na.
15. A process for preparing a compound of formula VII

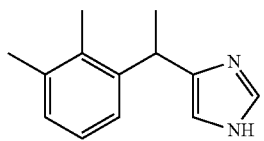

VII or a suitable salt thereof, comprising:
providing a compound of formula V using the process of claim 7,
reacting the compound of formula V to form a compound of formula VIII

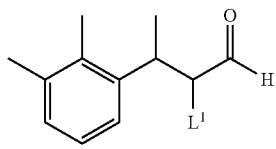

VIII wherein L¹ represents a suitable leaving group; and
(III) reacting the compound of formula VIII in the presence of (a) a source of formamidine, or
(b) formamide,
to form the compound of formula VII or the suitable salt thereof.

16. A process of claim 15, further comprising isolating and optionally purifying the compound of formula VIII.
17. A compound of claim 12, wherein Z represents Na.
18. A process of claim 13, wherein Z represents Na.
19. A process for preparing a compound of formula VII

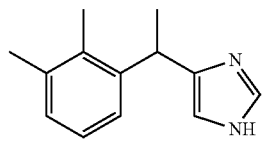

VII or a suitable salt thereof, comprising:
(I) providing a compound of formula I using a process of claim 1,

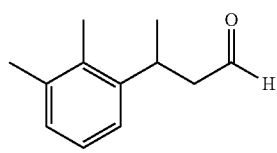

V (II) preparing a compound of formula V by reacting the compound of formula I with a suitable reducing agent;
(III) reacting the compound of formula V to form a compound of formula VIII

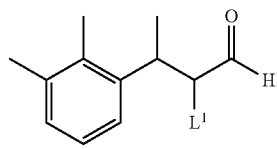

VIII wherein L¹ represents a suitable leaving group; and
(IV) reacting the compound of formula VIII in the presence of
(a) a source of formamidine, or
(b) formamide,
to form the compound of formula VII or the suitable salt thereof.

* * * * *